United States Patent [19]

Bardy

[11] Patent Number: 5,630,834
[45] Date of Patent: May 20, 1997

[54] ATRIAL DEFIBRILLATOR WITH MEANS FOR DELIVERING THERAPY IN RESPONSE TO A DETERMINATION THAT THE PATIENT IS LIKELY ASLEEP

[75] Inventor: Gust H. Bardy, Seattle, Wash.

[73] Assignee: Medtronic, Inc., Minneapolis, Minn.

[21] Appl. No.: 434,899

[22] Filed: May 3, 1995

[51] Int. Cl.$^6$ ........................................... A61N 1/39
[52] U.S. Cl. ........................ 607/5; 607/6; 607/19
[58] Field of Search ..................... 607/4, 5, 6, 19

[56] References Cited

U.S. PATENT DOCUMENTS

| | | |
|---|---|---|
| 3,738,370 | 6/1973 | Charms . |
| 4,316,472 | 2/1982 | Mirowski . |
| 4,375,817 | 3/1983 | Engle . |
| 4,384,585 | 5/1983 | Zipes . |
| 4,577,633 | 3/1986 | Berkovits . |
| 4,587,970 | 5/1986 | Holley . |
| 4,726,380 | 2/1988 | Vollmann . |
| 4,727,877 | 3/1988 | Kallok . |
| 4,800,883 | 1/1989 | Winstrom . |
| 4,830,006 | 5/1989 | Haluska . |
| 4,880,005 | 11/1989 | Pless . |
| 4,922,930 | 5/1990 | Adkins et al. .............. 607/19 |
| 4,949,719 | 8/1990 | Pless . |
| 4,953,551 | 9/1990 | Mehra . |
| 5,117,824 | 6/1992 | Keimel . |
| 5,143,065 | 9/1992 | Adkins . |
| 5,163,427 | 11/1992 | Keimel . |
| 5,165,403 | 11/1992 | Mehra . |
| 5,188,105 | 2/1993 | Keimel . |
| 5,233,984 | 8/1993 | Thompson .............................. 607/19 |
| 5,269,298 | 12/1993 | Adams . |
| 5,292,338 | 3/1994 | Bardy . |
| 5,342,404 | 8/1994 | Alt et al. ...................... 607/6 |
| 5,354,317 | 10/1994 | Alt . |
| 5,370,667 | 12/1994 | Alt ............................. 607/19 |

OTHER PUBLICATIONS

Olson et al., "Onset and Stability for Ventricular Tachyarrhythmia Detection in an Implantable Pacer-Cardioverter-Defibrillator", in Computers in Cardiology, Oct. 7–10, 1986, IEEE Computer Society Pres, pp. 167–170.

Arzbaecher et al. "Automatic Tachycardia Recognition", in PACE, May/Jun. 1984, pp. 541–547.

*Primary Examiner*—William E. Kamm
*Assistant Examiner*—George R. Evanisko
*Attorney, Agent, or Firm*—Reed A. Duthler; Harold R. Patton

[57] ABSTRACT

An automatic atrial defibrillator which includes a mechanism for sensing the occurrence of atrial fibrillation in a patient's heart and in response thereto delivers an atrial defibrillation pulse. The device also has the ability to determine whether the patient is likely to be asleep. Defibrillation pulses which are at energy levels which would normally be painful to the patient are delivered only in response to occurrences of atrial fibrillation while the patient is determined to likely be asleep. Defibrillation pulses at lower, non-painful levels may be delivered while the patient is not determined to be asleep.

12 Claims, 3 Drawing Sheets

ATRIAL DEFIBRILLATOR WITH MEANS FOR DELIVERING THERAPY IN RESPONSE TO A DETERMINATION THAT THE PATIENT IS LIKELY ASLEEP

BACKGROUND OF THE INVENTION

The present invention relates to medical stimulators and leads generally, and more particularly to implantable atrial defibrillators.

In the context of an implantable atrial defibrillator, it is generally believed desirable to reduce defibrillation energy thresholds. Because it is anticipated that such devices will likely deliver defibrillation pulses frequently, reduced energy thresholds are perceived as necessary in order to reduce the pain associated with atrial defibrillation pulses to an acceptable level. In the context of proposed prior art atrial defibrillators, a desirable atrial defibrillation threshold is generally stated to be 2 joules or less, preferably 1 joule or less. Numerous patents and applications, attempt to accomplish this goal by optimizing the atrial defibrillation electrode system. Nonetheless, the goal of a defibrillation of an atrial defibrillation lead system which will reliably accomplish such low defibrillation thresholds in all patients remains a difficult one.

One presently pending U.S. patent application Ser. No. 08/293,769, for an Atrial Defibrillator and Method of Use, filed Aug. 19, 1994 by Min et al. discloses an electrode system which appears to generally accomplish a desirably low atrial defibrillation threshold. However, the disclosed electrode system requires multiple atrial defibrillation electrodes to accomplish this result. The simpler right atrium to coronary sinus/great vein pathway, disclosed in U.S. Pat. No. 5,165,403, issued to Mehra provides a desirably low threshold in some patients, but in others requires substantially higher energy levels. The right ventricle to subcutaneous electrode system disclosed in U.S. Pat. No. 5,292,338, issued to Bardy provides the simplest electrode system, allowing use of the same electrodes for atrial and ventricular defibrillation, but requires higher energy levels than desired for atrial defibrillation. The cited Min et al application and the cited Mehra and Bardy patents are incorporated herein by reference in their entireties.

SUMMARY OF THE INVENTION

The present invention is directed toward the provision of a defibrillator particularly optimized for use in defibrillation of the atrium without causing unnecessary pain. Rather than pursuing the elusive goal of a lead system or pulse regimen which provides reliable defibrillation at shock levels which are not painful to the patient, e.g. about one joule or less, an atrial defibrillator according to the present invention may deliver higher energy shocks, e.g. several joules or more, in response to detection of atrial defibrillation. However, rather than delivering these higher energy shocks immediately in response to each detection of the occurrence of atrial fibrillation as taught in the prior art, a defibrillator according to the present invention instead conditions delivery of such these higher energy defibrillation shocks until circumstances indicate that the patient is likely asleep.

Delaying delivery of a defibrillation pulse until the patient is asleep provides a safe and workable method of minimizing pain associated with atrial defibrillation pulses as a result of two factors. First, unlike ventricular fibrillation, atrial fibrillation is not immediately harmful if untreated. Thus, treatment can practically be delayed for a period of hours after detection. Second, in most cases the patient retains no memory of pain associated with such higher energy shocks delivered while the patient is asleep. Thus, the present invention provides an atrial defibrillation therapy that is perceived as painless by the patient, even if the patient's defibrillation threshold requires pulse energy levels which would normally be associated with pain.

Detection of the fact that the patient is sleeping can be accomplished using methods and apparatus known to the art. For example, a real time clock, in conjunction with a physical activity sensor may be employed to detect the sleep state as in U.S. Pat. No. 5,143,065, incorporated herein by reference in its entirety. A posture sensor as disclosed in U.S. Pat. No. 5,354,317, issued to Alt, in U.S. Pat. No. 5,233,984, issued to Thompson or in U.S. patent application Ser. No. 08/413,736, filed by Sheldon on Mar. 30, 1995 all incorporated herein by reference in their entireties may be used alternatively, or in conjunction with the physical activity sensor and clock to detect the sleep state.

Preferably, the device is configured to perform both atrial and ventricular defibrillation or cardioversion. The embodiment of the invention disclosed in the present application is based upon the device disclosed in the above-cited Min et al application, the relevant subject matter of which has been included below, to which the invention has been added. However, it is believed that the invention may be workably included in any of the various implantable atrial defibrillators disclosed in any of the patents cited herein, or in other similar devices.

DETAILED DESCRIPTION OF THE PREFERRED EMBODIMENT

Figure 1:
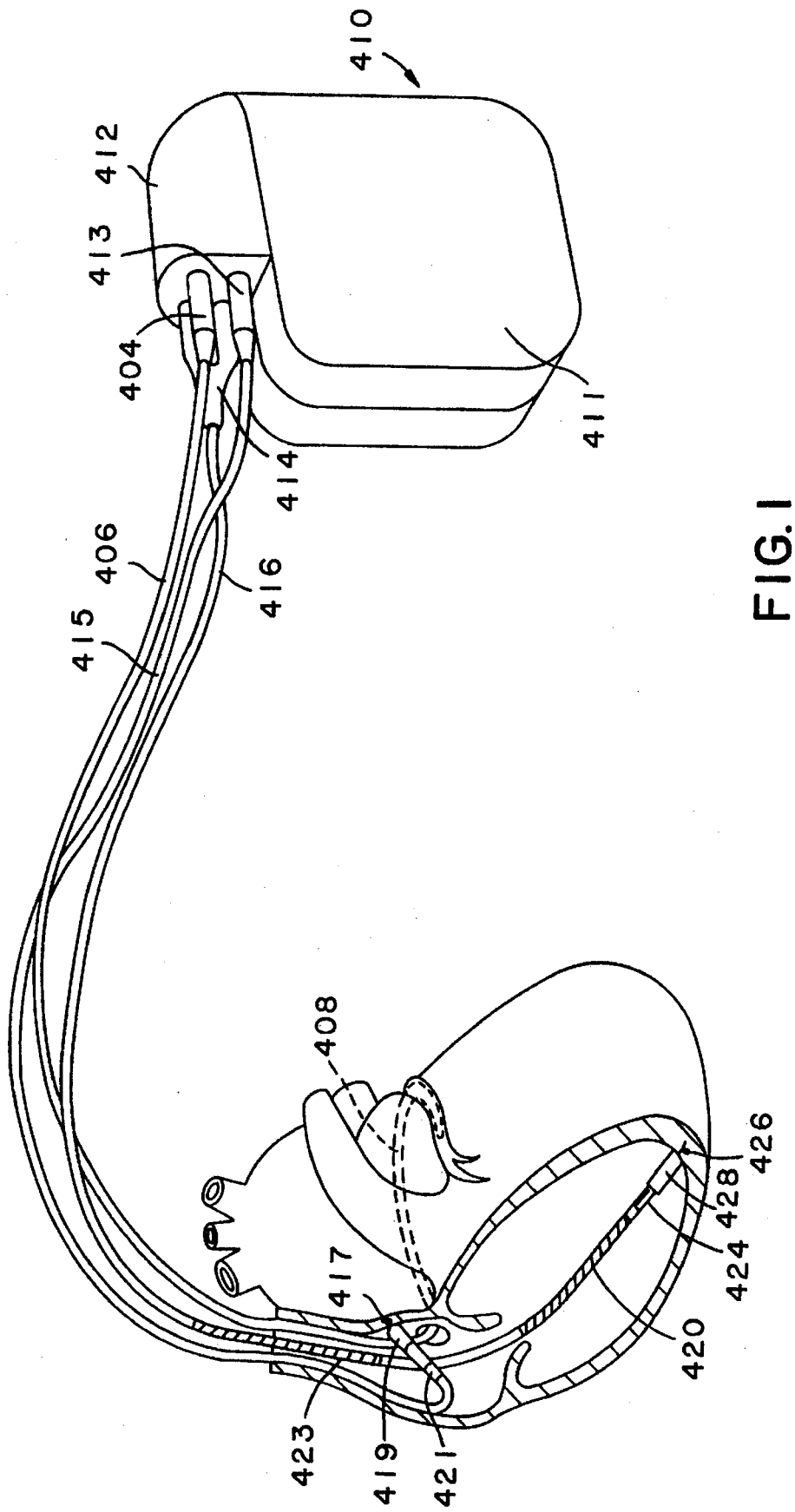
FIG. 1 illustrates a first embodiment of an implantable defibrillator and leads according to the present invention.

FIG. 1 illustrates a defibrillator and lead set according to the present invention. The ventricular lead is similar to the lead disclosed in the above cited '338 patent issued to Bardy, with the addition of a second defibrillation electrode for location in the coronary sinus. The ventricular lead includes an elongated insulative lead body 416, carrying four parallel, mounted within a four lumen tubular insulative sheath. Located adjacent the distal end of the lead are a ring electrode 424, an extendable helix electrode 426, mounted retractably within an insulative electrode head 428, and an elongated coil electrode 420. An additional elongated coil electrode 423 is located proximal to electrode 420, spaced to allow placement in the right atrium/SVC. Each of the electrodes is coupled to one of the coiled conductors within the lead body 416. Electrodes 424 and 426 are employed for cardiac pacing and for sensing ventricular depolarizations.

At the proximal end of the lead is a bifurcated connector 414 which carries four electrical connectors, each coupled to one of the coiled conductors. The defibrillation electrodes 420 and 423 may be fabricated from platinum, platinum alloy or other materials known to be usable in implantable defibrillation electrodes and may conveniently be about 5 cm in length and about 10 cm or greater in length, respectively. The atrial/SVC lead includes an elongated insulative lead body 415, carrying two concentric coiled conductors, separated from one another by a tubular insulative sheath, corresponding to the structure of the commercially available atrial pacing leads. Located adjacent the J-shaped distal end of the lead are a ring electrode 421 and an extendable helix electrode 417, mounted retractably within an insulative electrode head 419. Each of the electrodes is coupled to one of the coiled conductors within the lead body 15. Electrodes 417 and 421 are employed for atrial pacing and for sensing atrial depolarizations. At the proximal end of the lead is a bipolar, in-line connector 413 which carries two electrical connectors, each coupled to one of the coiled conductors.

The coronary sinus lead takes the form of the coronary sinus lead disclosed in the above cited '338 patent issued to Bardy. The lead includes an elongated insulative lead body 406, carrying one coiled conductor, coupled to an elongated coiled defibrillation electrode 408. Electrode 408, illustrated in broken outline, is located within the coronary sinus and great vein of the heart. At the proximal end of the lead is a connector plug 404 which carries an electrical connector, coupled to the coiled conductor. The coronary sinus/great vein electrode 408 may be about 5 cm in length.

An implantable pacemaker/cardioverter/defibrillator 410 is shown in combination with the leads, with the lead connector assemblies 404, 413 and 414 inserted into the connector block 412. Optionally, insulation of the outward facing portion of the housing 411 of the pacemaker/cardioverter/defibrillator 410 may be provided using a plastic coating, for example parylene or silicone rubber, as is currently employed in some unipolar cardiac pacemakers. However, the outward facing portion may instead be left uninsulated, or some other division between insulated and uninsulated portions may be employed. The uninsulated portion of the housing 411 optionally serves as a subcutaneous defibrillation electrode, used to defibrillate either the atria or ventricles.

Figure 2:
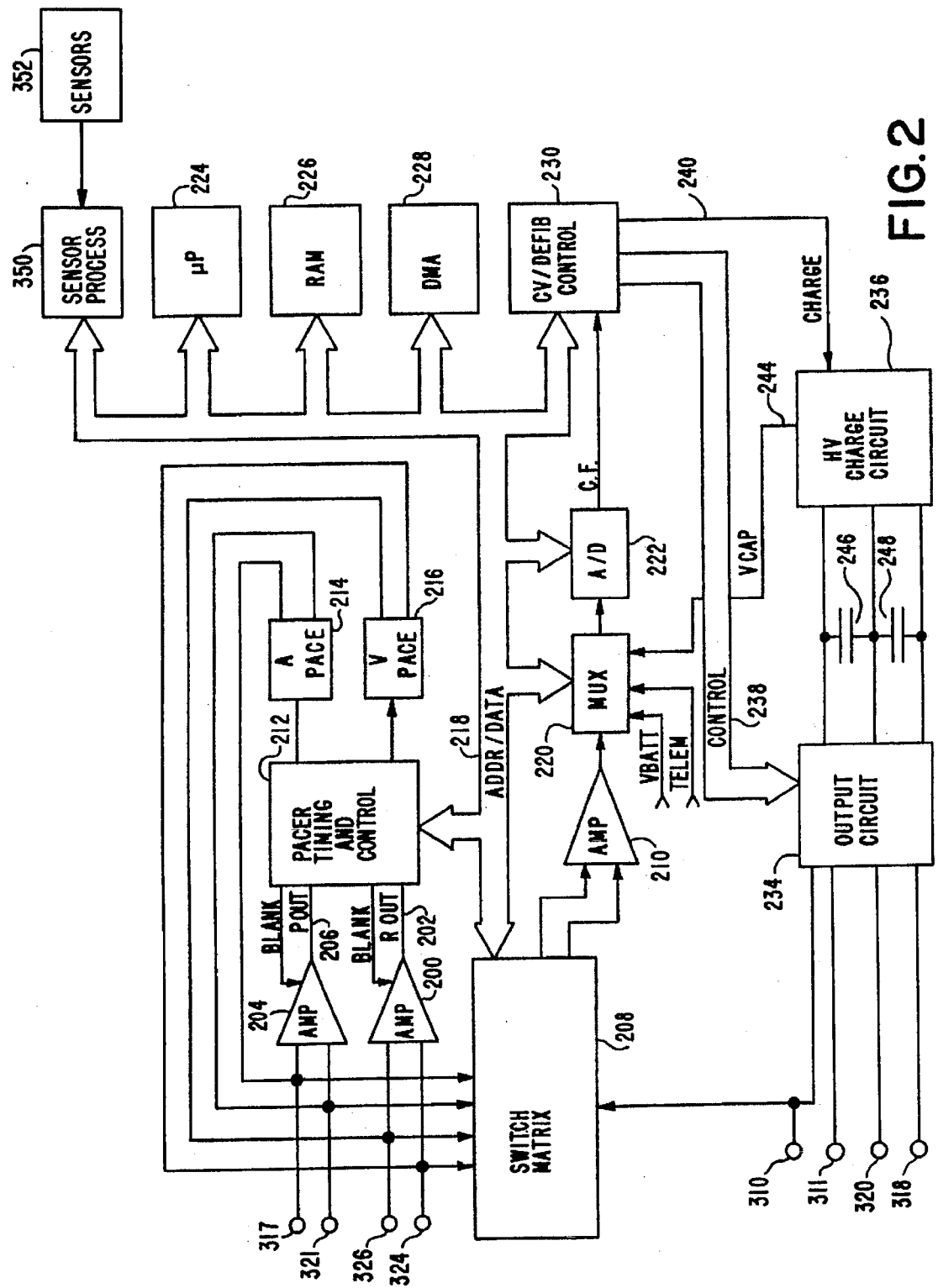
FIG. 2 illustrates a functional schematic diagram of an implantable pacemaker/cardioverter/defibrillator in which the invention may usefully be practiced in conjunction with the leads illustrated in FIG. 1.

FIG. 2 is a functional schematic diagram of an implantable pacemaker/cardioverter/defibrillator in which the present invention may usefully be practiced. This diagram should be taken as exemplary of the type of device in which the invention may be embodied, and not as limiting, as it is believed that the invention may usefully be practiced in a wide variety of device implementations, including cardioverter and defibrillators which do not provide anti-tachycardia pacing therapies.

The device as illustrated is provided with an electrode system including electrodes as illustrated in FIG. 1. If the electrode configuration of FIG. 1 is employed, the correspondence to the illustrated electrodes is as follows. Optional electrode 310 corresponds to electrode 411, and is the uninsulated portion of the housing of the implantable pacemaker/cardioverter/defibrillator. Electrode 320 corresponds to electrode 420 and is a defibrillation electrode located in the right ventricle. Electrode 311 corresponds to electrode 423, and is located in the right atrium and SVC. Electrode 318 corresponds to electrode 408 and is a defibrillation electrode located in the coronary sinus and great vein. Electrodes 324 and 326 correspond to electrodes 424 and 426, and are used for sensing and pacing in the ventricle. Electrodes 317 and 321 correspond to electrodes 417 and 419 and are used for pacing and sensing in the atrium.

Electrodes 310, 311, 318 and 320 are coupled to high voltage output circuit 234. High voltage output circuit 234 includes high voltage switches controlled by CV/defib control logic 230 via control bus 238. The switches within circuit 234 control which electrodes are employed and which are coupled to the positive and negative terminals of the capacitor bank including capacitors 246 and 248 during delivery of the defibrillation pulses.

Electrodes 424 and 326 are located on or in the ventricle and are coupled to the R-wave amplifier 200, which preferably takes the form of an automatic gain controlled amplifier providing an adjustable sensing threshold as a function of the measured R-wave amplitude. A signal is generated on R-out line 202 whenever the signal sensed between electrodes 612 and 614 exceeds the present sensing threshold.

Electrodes 317 and 321 are located on or in the atrium and are coupled to the P-wave amplifier 204, which preferably also takes the form of an automatic gain controlled amplifier providing an adjustable sensing threshold as a function of the measured P-wave amplitude. A signal is generated on P-out line 206 whenever the signal sensed between electrodes 617 and 621 exceeds the present sensing threshold. The general operation of the R-wave and P-wave amplifiers 200 and 204 may correspond to that disclosed in U.S. Pat. No. 5,117,824, by Keimel, et al., issued Jun. 2, 1992, for an Apparatus for Monitoring Electrical Physiologic Signals, incorporated herein by reference in its entirety.

Switch matrix 208 is used to select which of the available electrodes are coupled to wide band (0.5–200 Hz) amplifier 210 for use in digital signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known in the prior art. An exemplary apparatus for accomplishing pacing, cardioversion and defibrillation functions is as follows. The pacer timing/control circuitry 212 includes programmable digital counters which control the basic time intervals associated with DDD, VVI, DVI, VDD, AAI, DDI and other modes of single and dual chamber pacing well known to the art. Circuitry 212 also controls escape intervals associated with anti-tachyarrhythmia pacing in both the atrium and the ventricle, employing any anti-tachyarrhythmia pacing therapies known to the art.

Intervals defined by pacing circuitry 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 226, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are reset upon sensing of R-waves and P-waves as indicated by a signals on lines 202 and 206, and in accordance with the selected mode of pacing on timeout trigger generation of pacing pulses by pacer output circuitry 214 and 216, which are coupled to electrodes 317, 321, 324 and 326. The escape interval counters are also reset on generation of pacing pulses, and thereby control the basic timing of cardiac pacing functions, including anti-tachyarrhythmia pacing. The durations of the intervals defined by the escape interval timers are determined by microprocessor 224, via data/address bus 218. The value of the count present in the escape interval counters when reset by sensed R-waves and P-waves may be used to measure the durations of R-R intervals, P-P intervals, P-R intervals and R-P intervals, which measurements are stored in memory 226 and used to detect the presence of tachyarrhythmias.

Microprocessor 224 operates as an interrupt driven device, and is responsive to interrupts from pacer timing/control circuitry 212 corresponding to the occurrence sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts.

For example, in response to a sensed or paced ventricular depolarization or R-wave, the intervals separating that R-wave from the immediately preceding R-wave, paced or sensed (R-R interval) and the interval separating the paced or sensed R-wave from the preceding atrial depolarization, paced or sensed (P-R interval) may be stored. Similarly, in response to the occurrence of a sensed or paced atrial depolarization (P-wave), the intervals separating the sensed P-wave from the immediately preceding paced of sensed atrial contraction (P-P Interval) and the interval separating the sensed P-wave from the immediately preceding sensed or paced ventricular depolarization (R-P interval) may be stored. Preferably, a portion of the memory 226 (FIG. 2) is configured as a plurality of recirculating buffers, capable of holding a preceding series of measured intervals, which may be analyzed in response to the occurrence of a pace or sense interrupt to determine whether the patient's heart is presently exhibiting atrial or ventricular tachyarrhythmia.

Detection of atrial or ventricular tachyarrhythmias, as employed in the present invention, may correspond to tachyarrhythmia detection algorithms known to the art. For example, presence of atrial or ventricular tachyarrhythmia may be confirmed by means of detection of a sustained series of short R-R or P-P intervals of an average rate indicative of tachyarrhythmia or an unbroken series of short R-R or P-P intervals. The suddenness of onset of the detected high rates, the stability of the high rates, or a number of other factors known to the art may also be measured at this time. Appropriate ventricular tachyarrhythmia detection methodologies measuring such factors are described in U.S. Pat. No. 4,726,380, issued to Vollmann, U.S. Pat. No. 4,880,005, issued to Pless et al. and U.S. Pat. No. 4,830,006, issued to Haluska et at., all incorporated herein by reference in their entireties. An additional set of tachycardia recognition methodologies is disclosed in the article "Onset and Stability for Ventricular Tachyarrhythmia Detection in an Implantable Pacer-Cardioverter-Defibrillator" by Olson et al., published in *Computers in Cardiology*, Oct. 7–10, 1986, IEEE Computer Society Press, pages 167–170, also incorporated herein in its entirety. However, one of the advantages of the present invention is that it is believed practicable in conjunction with most prior art tachycardia detection algorithms. Atrial fibrillation detection methodologies in particular are disclosed in Published PCT Application Serial No. US92/02829, Publication No. WO92/18198, by Adams et al., and in the article "Automatic Tachycardia Recognition", by Arzbaecher et al., published in PACE, May-June, 1984, pp. 541–547, both of which are incorporated by reference in their entireties. In the context of the present invention, however, the specific methodology employed to detect atrial fibrillation is not critical. The present invention is believed valuable in the context of devices which detect atrial fibrillation by any mechanism, including detection by means of physiologic sensors, atrial and/or ventricular electrograms, or otherwise. In the context of the present invention, detection of atrial fibrillation, in and of itself is insufficient to trigger delivery of an atrial defibrillation pulse at an energy level which would be expected to cause pain. The present invention adds to the above described known functions, the requirement that the device determine that the patient is likely to be asleep, as an additional prerequisite prior to triggering delivery of such a higher energy atrial defibrillation pulse. The present invention accomplishes this by incorporation of mechanisms already known to the art, but employed for determining that the patient is in a sleep state. Three basic criteria are proposed for use in determining if the patient is likely to be asleep, and these three criteria may be combined in any desirable combination.

The first criterion is that the time of day indicates that the patient is likely to be asleep. This criterion is tested by comparing the present time as indicated by the real time clock within the microprocessor 224 against a time based model of the patient's waking and sleeping cycle. The time based model may be programmed into the device by the physician or may be updated automatically as a function of the patient's sensed activity levels over time, as disclosed in the '065 patent issued to Adkins, cited above. In this context, the sensors 352 may include a piezo electric activity sensor or other physiologic sensor indicative of physiologic activity. The output of the sensor is provided to the sensor processing circuitry 350, and by means of address/data buss 218, to microprocessor 224.

The second criterion to be considered by the device is whether the patient is currently exhibiting a low level of physical activity, consistent with sleep, while atrial fibrillation is present. A low current level of physical activity may correspondingly be detected by a means of a piezo electric sensor, as discussed above.

The third criterion that might be employed is whether the patient is prone at the time atrial fibrillation is present. In particular, the device may determine whether, the patient has exhibited a reclining posture for a substantial period of time, as indicated by the real time clock. A postural sensor and the processing circuitry corresponding to any of those in the cited Alt or Thompson patents or the Sheldon application, may be employed to accomplish this result. These three criteria may be combined in any desired manner.

For example, while atrial fibrillation is present it may be required that the patient exhibit a present low rate of physical activity, the time of day be consistent with the sleep state, and that a postural sensor indicate the patient has been in a reclining position for an hour or more. Alternatively, any two of the criteria may be combined together as prerequisites for triggering delivery of an atrial defibrillation pulse, or any of the criteria may be employed alone. The more criteria employed for determining that the patient is likely to be sleeping, the less likely a defibrillation shock will be delivered while the patient is awake.

In response to a determination that atrial fibrillation is present while the patient is asleep, a device according to the present invention triggers delivery of a defibrillation pulse of sufficient amplitude to terminate atrial fibrillation. This may be the only defibrillation therapy provided by the device. As an alternative, the device may employ a dual strategy for treatment of atrial fibrillation. For example, in response to detecting of atrial fibrillation while the patient is not likely to be in a sleep state, the device may deliver defibrillation pulses at an energy level chosen to be tolerable by the patient, even if such pulses do not consistently defibrillate the atrium or may attempt other therapies painless to the patient. For example, a defibrillation pulse of one joule or less may be applied. Alternatively or in addition, anti-tachycardia pacing pulses may be applied, on the chance that the detected fibrillation is in fact a high rate atrial flutter, which may sometimes be terminated by high rate atrial pacing. If the painless therapy or therapies are successful in terminating the atrial fibrillation, no further therapy need be pursued. If, on the other hand, the painless therapies are unsuccessful in terminating the therapy, the device may thereafter wait until it detects simultaneous occurrence of atrial fibrillation and a likely sleep state, and in response thereto deliver a higher energy defibrillation pulse, at a level known to be reliably capable of terminating the atrial fibrillation. In a device functioning in this manner, battery consumption may be substantially reduced, if episodes of atrial fibrillation can often be terminated by the lower energy therapies.

In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties may also be used.

In the event that generation of a cardioversion or defibrillation pulse is required, microprocessor 224 employs an escape interval counter to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246 and 248 via charging circuit 236, under control of high voltage charging control lines 240 and 242. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization.

One embodiment of an appropriate system for delivery and synchronization of ventricular cardioversion and defibrillation pulses and for controlling the timing functions related to them is disclosed in more detail in commonly assigned U.S. Pat. No. 5,188,105 by Keimel, issued Feb. 23, 1993, incorporated herein by reference in its entirety. Embodiments of appropriate systems for delivery and synchronization of atrial cardioversion and defibrillation pulses and for controlling the timing functions related to them are disclosed in more detail in U.S. Pat. No. 5,269,298 by Adams et al. , issued Dec. 14, 1993 and in U.S. Pat. No. 4,316,472 by Mirowski et al., issued Feb. 23, 1982, both incorporated herein by reference in their entireties. However, any known cardioversion or defibrillation pulse control circuitry is believed usable in conjunction with the present invention. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al., cited above, and in U.S. Pat. No. 4,375,817, issued to Engle et al., all incorporated herein by reference in their entireties may also be employed.

In the illustrated device, delivery of the cardioversion or defibrillation pulses is accomplished by output circuit 234, under control of control circuitry 230 via control bus 238. Output circuit 234 determines whether a monophasic or biphasic pulse is delivered, the polarity of the electrodes and which electrodes are involved in delivery of the pulse. Output circuit 234 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, incorporated by reference in its entirety.

An example of circuitry which may be used to control delivery of monophasic pulses is set forth in commonly assigned U.S. Pat. No. 5,163,427, by Keimel, issued Nov. 17, 1992, also incorporated herein by reference in its entirety. However, output control circuitry as disclosed in U.S. Pat. No. 4,953,551, issued to Mehra et al. on Sep. 4, 1990 or U.S. Pat. No. 4,800,883, issued to Winstrom on Jan. 31, 1989 both incorporated herein by reference in their entireties, may also be used in conjunction with a device embodying the present invention for delivery of biphasic pulses.

In the event that, as in FIG. 1, both atrial and ventricular defibrillation are available, ventricular defibrillation may be accomplished using higher pulse energy levels than required for atrial defibrillation and may employ the same or a different electrode set. For example, electrodes 310, 311, 318 and 320 or only electrodes 311, 318 and 320 may be employed for atrial defibrillation. Electrodes 311, 320 and 310 might be employed for ventricular defibrillation, with electrode 311 (right atrium/SVC) coupled to electrode 310 (device housing). Alternatively, electrodes 310, 318 and 320 may be employed, with electrode 318 (coronary sinus/great vein) coupled to electrode 310. As a further alternative, electrodes 311, 310, 318 and 323 might all be employed for ventricular defibrillation, with electrodes 310, 311 and 323 coupled in common. As yet another alternative, only electrodes 310 and 320 might be employed for ventricular defibrillation, with electrodes 311 and 318 used for treating atrial fibrillation.

One possible embodiment of the invention employs only the right atrial/SVC electrode 311, the coronary sinus/great vein electrode 318 and the right ventricular electrode 320. During atrial defibrillation, electrodes 320 and 318 are coupled in common with one another, and the atrial defibrillation pulse is delivered between these electrodes and electrode 311. During ventricular defibrillation, electrodes 311 and 318 are coupled in common with one another, and the ventricular defibrillation pulse is delivered between these electrodes and electrode 320. This particular set of electrodes thus provides optimized defibrillation pulse regimens for both atrial and ventricular defibrillation, by simply switching the connection of the coronary sinus/great vein electrode.

In modern implantable cardioverter/defibrillators, the particular therapies are programmed into the device ahead of time by the physician, and a menu of therapies is typically provided. For example, on initial detection of an atrial or ventricular tachycardia, an anti-tachycardia pacing therapy may be selected and delivered to the chamber in which the tachycardia is diagnosed or to both chambers. On redetection of tachycardia, a more aggressive anti-tachycardia pacing therapy may be scheduled. If repeated attempts at anti-tachycardia pacing therapies fail, a higher level cardioversion pulse may be selected thereafter. Therapies for tachycardia termination may also vary with the rate of the detected tachycardia, with the therapies increasing in aggressiveness as the rate of the detected tachycardia increases. For example, fewer attempts at anti-tachycardia pacing may be undertaken prior to delivery of cardioversion pulses if the rate of the detected tachycardia is above a preset threshold. The references cited above in conjunction with descriptions of prior art tachycardia detection and treatment therapies are applicable here as well.

In the event that atrial or ventricular fibrillation is identified, the typical therapy will be delivery of a high amplitude defibrillation pulse, typically in excess of 10 joules in the case of ventricular fibrillation and about 1 joule or less in the case of atrial defibrillation. Lower energy levels will be employed for cardioversion. As in the case of currently available implantable pacemaker/cardioverter/defibrillators, and as discussed in the above-cited references, it is envisioned that the amplitude of the defibrillation pulse may be incremented in response to failure of an initial pulse or pulses to terminate fibrillation. Prior art patents illustrating such pre-set therapy menus of anti-tachyarrhythmia therapies include the above-cited U.S. Pat. No. 4,830,006, issued to Haluska, et al., U.S. Pat. No. 4,727,380, issued to Vollmann et al. and U.S. Pat. No. 4,587,970, issued to Holley et al.

Figure 3:
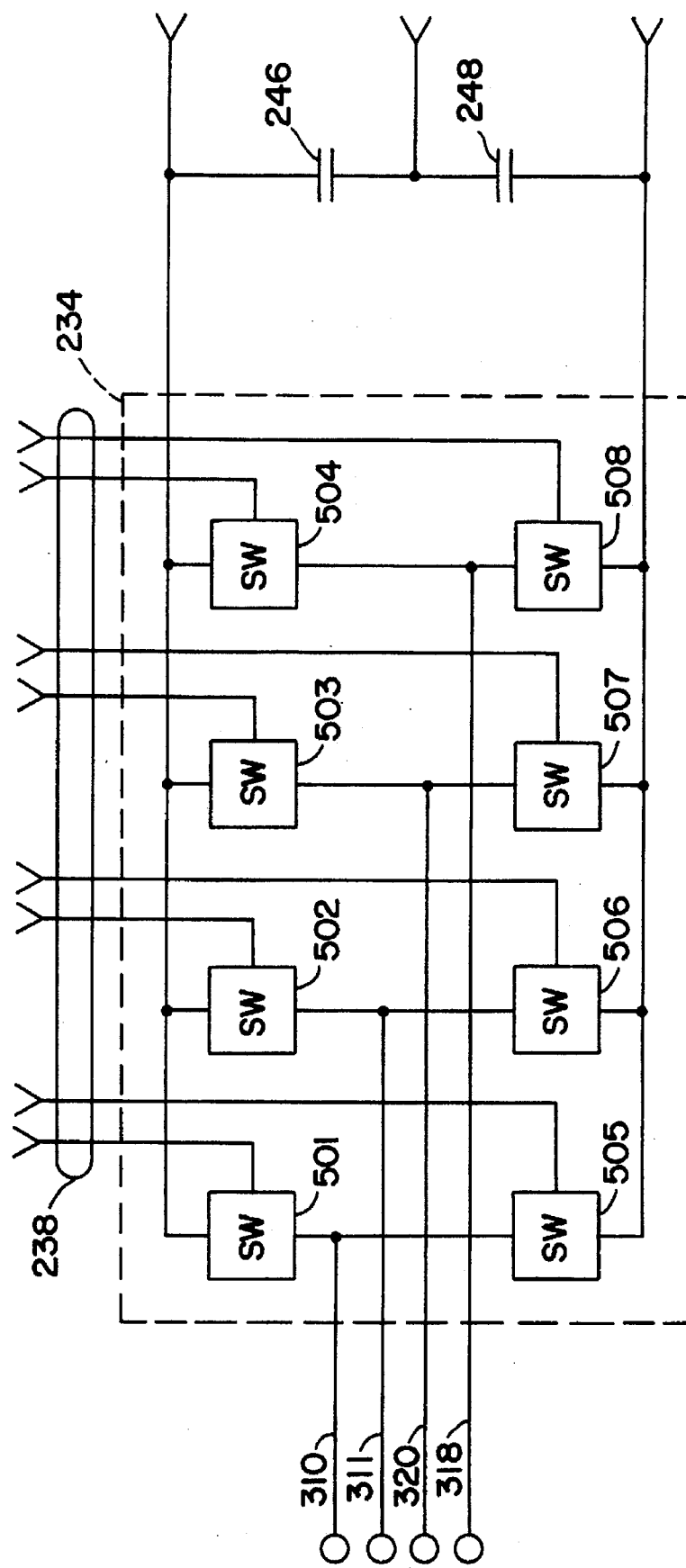
FIG. 3 illustrates a functional schematic diagram of the high voltage output circuit of the implantable pacemaker/cardioverter/defibrillator illustrated in FIG. 2.

FIG. 3 is a functional schematic diagram of switching circuitry which may be employed in high voltage output circuit 234, illustrated in FIG. 2. The circuitry includes eight high voltage switches 501, 502, 503, 504, 505, 506, 507 and 508, which are individually controlled by signals on control bus 238. These switches allow connection of any of the four electrodes 301, 311, 320 and 318 to either the positive or the negative terminal of the capacitor and comprising capacitors 246 and 248. As illustrated, any combination of electrodes may be selected, any polarities desired may be provided, and monophasic or biphasic pulses may be delivered, depending upon control signals on control bus 238. In the event that a reduced set of available electrode configurations is desired, the switching circuitry may be simplified. For example, if two electrodes (e.g. 318 and 320) are hard wired together, either in the connector block or in the device housing, one set of two switches (504, 508) may be deleted. Correspondingly, if only three electrodes are desired, (e.g. electrode 310 is deleted) a set of switches (501,505) may similarly be deleted. If only atrial defibrillation is desired, using only three electrodes both of these changes could be made, resulting in an output circuit employing only four switches and which corresponds to high voltage output circuits presently used in implantable ventricular defibrillators.

While the invention is disclosed above embodied in a dual chamber pacemaker/cardioverter/defibrillator, the invention may also be usefully practiced in substantially simpler devices. For example, the illustrated defibrillation electrodes may simply be coupled to an implantable atrial cardioverter as disclosed in U.S. Pat. No. 3,738,370, issued to Charms, or as disclosed in published PCT Application Serial No. US92/02829, Publication No. WO92/18198, by Adams et al, both of which are incorporated herein by reference in their entireties. A simple device of this type is believed workable in some patients. However, inclusion of the ability to detect and terminate ventricular tachycardias and fibrillation is believed of extreme importance in patients in whom delivery of atrial cardioversion or defibrillation pulses unintentionally initiates ventricular arrhythmias.

In conjunction with the above specification, we claim:

1. A device for delivering defibrillation pulses to a patient's atrium, comprising:

means for sensing atrial fibrillation;

means for determining that the patient is likely to be asleep; and means for delivering a defibrillation shock to the patient's atrium in response to the determination that said patient is likely to be asleep and upon sensing atrial fibrillation.

2. A device according to claim 1 wherein said delivering means further comprises means for delivering a lower energy level defibrillation shock to the patient's atrium in response to the determination that said patient is not likely to be asleep and upon sensing atrial fibrillation.

3. A device according to claim 1 wherein said delivering means further comprises means for delivering a first, painless therapy to the patient's atrium in response to the determination that said patient is not likely to be asleep and upon sensing atrial fibrillation.

4. A device according to claim 1 or claim 2 or claim 3 wherein said determining means comprises means for detecting the patient's activity level.

5. A device according to claim 1 or claim 2 or claim 3 wherein said determining means comprises means for detecting the patient's posture.

6. A device according to claim 1 or claim 2 or claim 3 wherein said determining means comprises means for determining time of day.

7. A method of delivering defibrillation pulses to a patient's atrium, comprising:

sensing atrial fibrillation;

determining that the patient is likely to be asleep; and delivering a defibrillation shock to the patient's atrium in response to the determination that said patient is likely to be asleep and upon the sensing of atrial fibrillation.

8. A method according to claim 7 further comprising the step of delivering a lower energy level defibrillation shock to the patient's atrium in response to the determination that said patient is not likely to be asleep and upon the sensing of atrial fibrillation.

9. A method according to claim 7 further comprising the step of delivering a first, painless therapy to the patient's atrium in response to the determination that said patient is not likely to be asleep and upon the sensing of atrial fibrillation.

10. A method according to claim 7 or claim 8 or claim 9 wherein said determining step comprises determining the patient's activity level.

11. A method according to claim 7 or claim 8 or claim 9 wherein said determining step comprises determining the patient's posture.

12. A method according to claim 7 or claim 8 or claim 9 wherein said determining step comprises determining time of day.

* * * * *